US009028505B2

(12) United States Patent
Witt

(10) Patent No.: US 9,028,505 B2
(45) Date of Patent: May 12, 2015

(54) METHOD AND APPARATUS FOR DRIVING A MEMBER

(71) Applicant: Biomet Manufacturing, LLC, Warsaw, IN (US)

(72) Inventor: Tyler D. Witt, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 93 days.

(21) Appl. No.: 13/712,107

(22) Filed: Dec. 12, 2012

(65) Prior Publication Data

US 2014/0163574 A1 Jun. 12, 2014

(51) Int. Cl.
| | |
|---|---|
| *A61B 17/00* | (2006.01) |
| *B25B 17/02* | (2006.01) |
| *A61B 17/88* | (2006.01) |
| *B25B 15/04* | (2006.01) |
| *B25B 17/00* | (2006.01) |
| *A61F 2/36* | (2006.01) |
| *A61F 2/30* | (2006.01) |
| *A61F 2/46* | (2006.01) |

(52) U.S. Cl.
CPC ........... *A61B 17/8875* (2013.01); *A61F 2/3662* (2013.01); *A61F 2002/30471* (2013.01); *A61F 2002/3052* (2013.01); *A61F 2002/4638* (2013.01); *B25B 15/04* (2013.01); *B25B 17/00* (2013.01)

(58) Field of Classification Search
CPC .............................. A61B 17/8875; B25B 17/02
USPC ............ 606/104; 29/525.11; 81/57.26, 177.8, 81/177.9
See application file for complete search history.

(56) References Cited

U.S. PATENT DOCUMENTS

| | | | |
|---|---|---|---|
| 4,825,734 A | 5/1989 | Schwalbe et al. | |
| 6,378,402 B1 | 4/2002 | Kalomeris et al. | |
| 6,564,680 B1 | 5/2003 | Rinner et al. | |
| 6,922,870 B2 | 8/2005 | Tontz, Sr. | |
| 6,996,886 B1 | 2/2006 | Rinner | |
| 7,014,023 B1 | 3/2006 | Gauthier | |
| 7,156,216 B2 | 1/2007 | Gauthier | |
| 7,287,450 B1 * | 10/2007 | Liao ............................ | 81/177.9 |
| 7,413,065 B2 | 8/2008 | Gauthier | |
| 7,430,945 B2 | 10/2008 | Gauthier et al. | |
| 7,650,821 B2 | 1/2010 | Gauthier et al. | |
| 7,806,026 B2 | 10/2010 | Gauthier | |
| 7,849,766 B2 | 12/2010 | Sharifi-Mehr et al. | |
| 7,866,235 B2 | 1/2011 | Hi | |
| D634,844 S | 3/2011 | Bast et al. | |
| 7,913,594 B2 | 3/2011 | Gauthier et al. | |
| 7,922,719 B2 * | 4/2011 | Ralph et al. .................. | 606/79 |
| 7,987,745 B2 | 8/2011 | Gauthier et al. | |
| D646,384 S | 10/2011 | Gauthier et al. | |

(Continued)

OTHER PUBLICATIONS

Gauthier, Spinal Instruments—Speed Driver, Pistol Grip, Gauthier Biomedical Inc., www.gauthierbiomedical.com/products; 2 pgs. (2012).

(Continued)

*Primary Examiner* — Christopher Beccia
(74) *Attorney, Agent, or Firm* — Harness, Dickey

(57) ABSTRACT

A method and tool for driving a bit. The tool includes a handle extending along a longitudinal axis between a first end and a second end. The handle can be in a first configuration to provide a first drive ration. In a second configuration, such as a T-shaped configuration, a gear assembly can be disengaged to provide a second drive ratio for the bit driving system.

20 Claims, 3 Drawing Sheets

(56) References Cited

U.S. PATENT DOCUMENTS

| | | |
|---|---|---|
| D646,385 S | 10/2011 | Gauthier et al. |
| D646,386 S | 10/2011 | Miller et al. |
| D646,387 S | 10/2011 | Bast et al. |
| D646,783 S | 10/2011 | Bast et al. |
| D647,201 S | 10/2011 | Gauthier et al. |
| 8,037,790 B2 | 10/2011 | Gauthier |
| D648,433 S | 11/2011 | Bast et al. |
| D654,589 S | 2/2012 | Bast et al. |
| D655,002 S | 2/2012 | Bast et al. |
| 8,122,788 B2 | 2/2012 | Gauthier et al. |
| D655,815 S | 3/2012 | Miller et al. |
| D660,421 S | 5/2012 | Miller et al. |
| D663,025 S | 7/2012 | Bast et al. |
| 2010/0180732 A1* | 7/2010 | Gauthier et al. .................. 81/60 |

OTHER PUBLICATIONS

Benjamin et al., Collarless Polished Cemented Stem Surgical Technique (CPCS_ST_71380787), Smith & Nephew Orthopaedics GmbH, Germany, 24 pages (Dec. 2000).

* cited by examiner

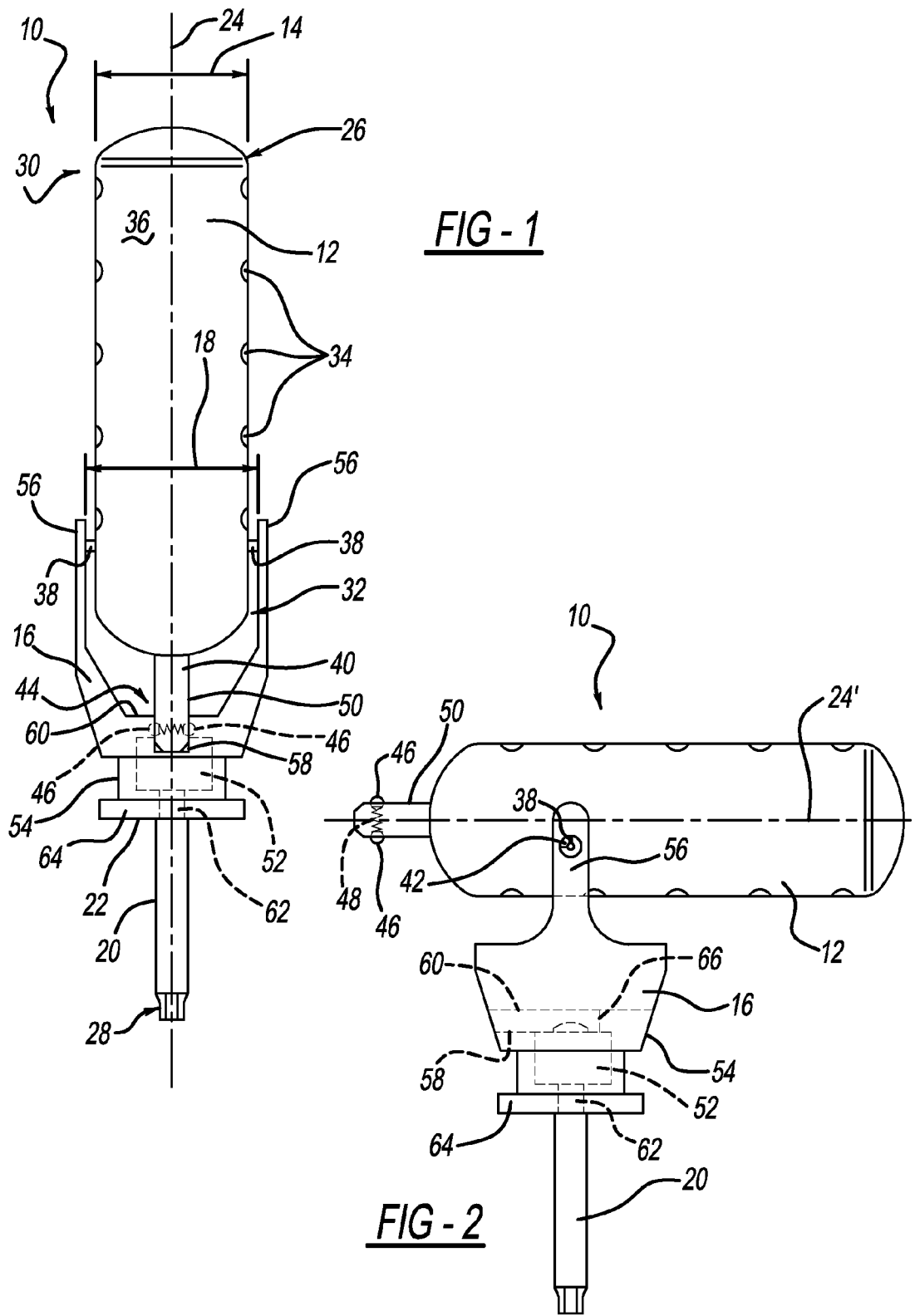

METHOD AND APPARATUS FOR DRIVING A MEMBER

FIELD

The present disclosure relates generally to surgical tools; and relates particularly to a drive system for driving a bit with manual operation.

BACKGROUND

This section provides background information related to the present disclosure which is not necessarily prior art.

Prosthetic devices can be implanted in a patient's body in a variety of ways and in a variety of locations. In reconstructive procedures of a hip joint, for example, defective bone tissue on both sides of the hip (e.g., femoral and acetabular) can be removed for subsequent implantation of a femoral and an acetabular prosthesis. With respect to the femoral prosthesis, a proximal portion, including a femoral head, of a femur can be resected to provide access for receipt of a femoral prosthesis. The femoral prosthesis may be implanted within the IM canal, such as coaxially, of the resected femoral bone. The femoral prosthesis is secured, using, for example, trochanteric bolts, wires, nails, etc. Likewise, an acetabulum may be reamed for receipt of an acetabular cup of the acetabular prosthesis. The acetabular cup may also be secured within the reamed acetabulum using various fastening devices. In current practice, multiple tools are used to prepare the bones and attach the prosthetic components. It is, therefore, advantageous to incorporate multiple functions into a single handle to reduce part inventory, while also increasing usability and surgical efficiency.

SUMMARY

This section provides a general summary of the disclosure, and is not a comprehensive disclosure of its full scope or all of its features.

In one form, the present disclosure provides a bit driving system including a bit to be driven. The system can also include a handle extending along a longitudinal axis between a first end and a second end. A first bit connection portion is arranged at least at one of the first end or the second end to selectively engage the handle in an axial configuration, while a second bit connection portion intermediate the first end and the second end selectively engages the handle in a T-shaped configuration. The system can also include a gear assembly selectively engaging the handle at the first bit connection portion to provide a first drive ratio for the bit driving system when in the axial configuration. When in the T-shaped configuration, the gear assembly is disengaged from the handle to provide a second drive ratio for the bit driving system.

In another form, the present disclosure provides a bit driving system including a handle extending along a longitudinal axis between a first end and a second end. The system can also include a pin extending from one of the first end or second end. A pivoting mechanism protrudes from the handle between the first and second ends. The system can also include a cap fixedly joined to the handle at the pivoting mechanism. A gear assembly in the cap selectively engages and disengages the pin. The bit driving system provides a first drive ratio for the bit when the pin and gear assembly are engaged and a second drive ratio for the bit when the pin and gear assembly are disengaged.

In yet another form, the present disclosure provides a method for driving a bit with a bit driving tool having a longitudinal axis and a handle with a handle axis rotatable between an axial configuration and a T-handle configuration. In the axial configuration the handle axis extends along the longitudinal axis and in the T-handle configuration the handle axis extends transverse to the longitudinal axis. The method can include selecting a first drive ratio. The method can also include pivoting the handle of the bit driving tool to the T-handle configuration or to the axial configuration to achieve the selected first drive ratio. The method can include rotating the bit driving tool about the longitudinal axis at the first drive ratio to drive the bit and secure a first fastener.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a side view of a modular handle constructed in accordance with the teachings of the present disclosure and shown in an axial configuration;

FIG. 2 is a side view of a modular handle constructed in accordance with the teachings of the present disclosure and shown in a T-handle configuration;

Corresponding reference numerals indicate corresponding parts throughout the several views of the drawings.

DETAILED DESCRIPTION

Figure 3:
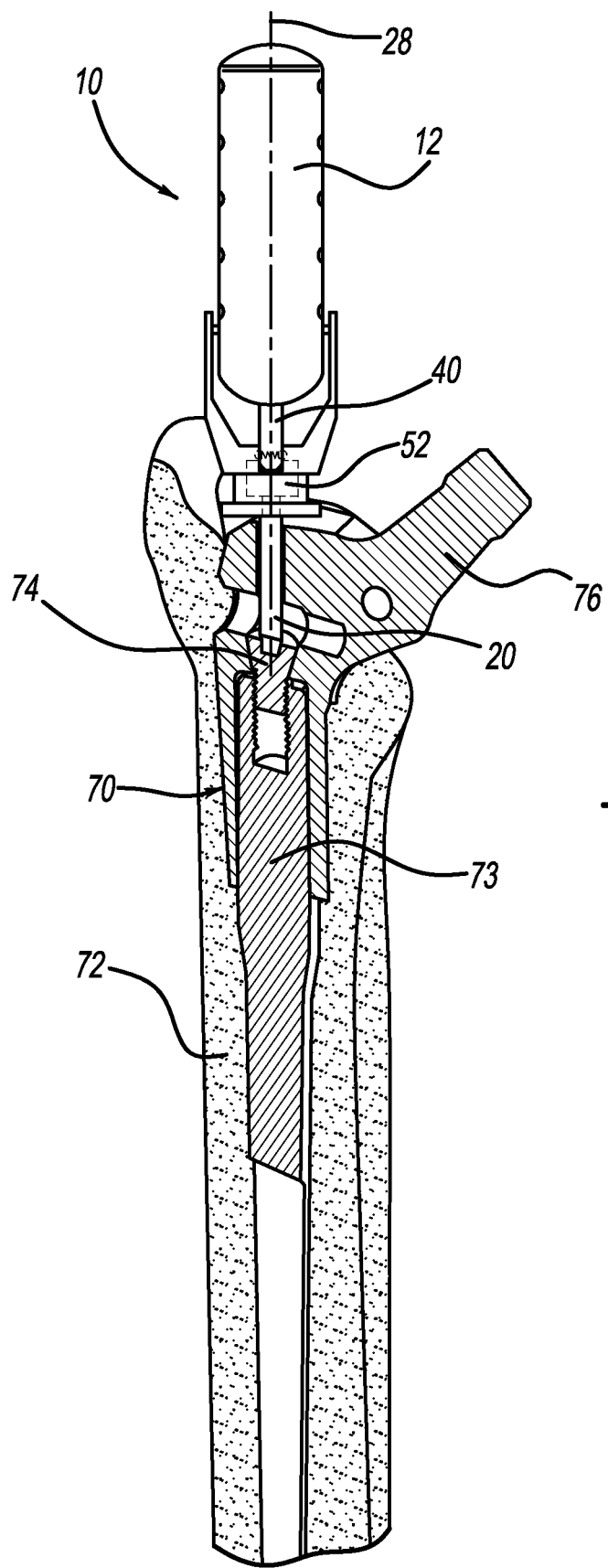
FIG. 3 is a side view of the modular handle of FIG. 1 in an operative position in association with a femoral prosthesis.

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-4, a method and apparatus is disclosed according to the present teachings for providing a modular handle for driving various fasteners in a prosthesis. However, the apparatus and method may also be used for a plurality of other procedures. For example, the instrument may be used as a precision driver for fasteners requiring small attachment mechanisms, a high number of handle revolutions, and/or a large amount of torque. The fasteners can used to interconnect any selected portion, such as any construction or assemblage system. Therefore, it will be understood that the following discussions are not intended to limit the scope of the present teachings or claims herein. This is also understood to mean that the driver can be used in both medical and non-medical procedures, such as, in an assembly procedure where fasteners are used.

Referring now to FIGS. 1 and 2 of the drawings, a bit driver can be a bit driving tool 10 is illustrated. Bit driving tool 10 is shown including an elongated body or handle 12 having an outer diameter 14, a cap 16 having an inner diameter 18, and a distal bit 20 extending downwardly from a lower end 22 of the cap 16. The inner diameter 18 of the cap 16 is shown to be greater than the outer diameter 14 of the handle 12. The bit driving tool 10, in at least one configuration, may extend substantially along a tool axis 24 between a proximal end 26 and a distal end 28 of the tool 10. The tool axis 24, however, is generally defined by the cap 16 and the bit 20.

The bit driving tool 10 may be manufactured of any suitable material for use as a precision tool, such as a metal, a hard polymer, a ceramic, or a composite. In one exemplary configuration, the bit driving tool 10 can be reusable and formed of a biocompatible material, such as a stainless steel, titanium, or the like, consistent with such purpose. Additionally, it will be appreciated that the bit driving tool 10 can be formed in any suitable fashion (e.g., casting, milling, etc.) and in any of various sizes and shapes to provide a drive system that can drive a bit by manual operation by a user, such as a human user.

The handle 12 may, at least in a first configuration, extend substantially along the tool axis 24 between a proximal handle end 30 and a distal handle end 32 and may include a plurality of gripping features 34 arranged about an external surface 36 of the handle 12. A pair of pivot pins 38 extends perpendicular to the tool axis 24 between the proximal and distal handle ends 30, 32 to engage the cap 16. A detent pin 40 extends from the distal handle end 32. The handle 12 may be substantially cylindrical between the proximal and distal handle ends 30, 32. The gripping features 34 may be integrally formed indentations so as to aid in retention in an operator's hand. In an alternate arrangement, the gripping features 34 may be machined features on the surface 36 of the handle 12 (e.g., knurl).

The pivot pins 38 may extend from the external surface 36 of the handle 12 so as to be rotatingly disposed in the cap 16. The pivot pins 38 in combination with the handle 12 and the cap 16 allow the handle 12 to change configurations from the first configuration to the a second configuration relative to at least the distal end 28. In particular, the pivot pins 38 may be sized so as to rotate within a pair of openings 42 within the cap 16. As shown more particularly in FIG. 2, the pivot pins 38 and openings 42 may have a keyed arrangement so as to allow the pivot pins 38 to rotate only a predetermined distance, such as, equivalent to a 90° rotation of the handle 12. In this way, for example, the handle 12 may be rotated such that a handle axis 24' is positioned at a right angle to the tool axis 24. It is understood, however, that the handle 12 can be rotated to any selected angle, such as about 45 degrees, about 60 degrees, etc. In the rotated configuration, the pivot pins 38 allow the bit 20 to be intermediate to the proximal and distal handle ends 30, 32. In the illustrated exemplary configuration, the driver 10 allows the handle 12 to selectively engage the bit 20 in a T-shaped handle (also referred to as a T-handle) configuration. As discussed above, the bit 20 either alone or with the cap 16 can be a bit connection portion. Furthermore, the rotation may also be 180° such that the head may rotate 90° either way from the axial configuration to the T-shaped handle configuration.

The pivot pins 38 are described as two separate members; however, it should be understood that a single piece extending through the handle 12 may alternately be used as a pivot member for the bit driving tool 10. Furthermore, the pivot pins 38 may include a feature for releasably retaining the handle 12 in either an axial or a T-shaped handle configuration (e.g., a magnetic feature, a fastener, or a detent mechanism). Accordingly, in either configuration there is a mechanism for securely retaining the handle 12 as required.

The detent pin 40 may extend a predetermined distance from the distal handle end 32 and may include a detent mechanism 44 for retaining the handle 12 in the axial configuration relative to the cap 16. The detent pin 40 may define at least a portion of the bit connection portion at the distal handle end 32 for selectively engaging the bit 20 in the axial configuration. As shown, the detent mechanism 44 may include a plurality of ball bearings 46 resiliently biased outwardly by a compression spring mechanism 48 so as to protrude outwardly from a surface 50 of the detent pin 40. The ball bearings 46 may engage the cap 16 for locking the handle 12 in the axial configuration. The detent pin 40 may also engage a gear assembly 52 located within the cap 16.

The cap 16 may include a body 54 for housing the gear assembly 52. A pair of spaced apart legs 56 extend from the body 54. A channel 58 can also extend at least partly through the body 54 at an upper end 60 thereof. A ratchet assembly 62 and a ratchet handle 64 are also provided at the lower end 22 of the body 54 of the cap 16 for engaging the distal bit 20. The body 54 of the cap 16 may also extend along the tool axis 24 and may have the legs 56 protruding upwardly from the upper end 60 of the cap 16 opposite the distal bit 20.

The legs 56 may have a predetermined length so as to be engageable with the pivot pins 38. Accordingly, the legs 56 may be spaced apart and may be a dimension larger than the outer diameter 14 of the handle 12. The inner diameter 18 of the cap 16 can be selected to allow an appropriate clearance between the legs 56 and the handle 12. In this way, the handle 12 may rotate freely between the axial and T-handle configurations, while the cap 16 remains aligned with the distal bit 20. The openings 42 may extend from the inner diameter 18 of the cap 16 through each of the legs 56 and include a feature for preventing rotation beyond a predefined limit, as shown.

The channel 58 may be a u-shaped groove for allowing the detent pin 40 to rotate into engagement with the gear assembly 52. The channel 58 may extend downwardly from the upper end 60 of the body 54 and may extend along a path perpendicular to the rotation of the handle 12 about the pivot pins 38. The channel 58 may also include a divot or widened opening (not shown) proximate a rear-most end 66 for receiving and seating the ball bearings 46. In this way, the detent mechanism 44 may removably retain the handle 12 in the axial configuration.

The gear assembly 52 may include a sun gear, a plurality of planetary gears, and/or a ring gear rotatingly engaged so as to provide a variable drive ratio between the handle 12 and the distal bit 20. In this way, the gear assembly 52 may be engaged to selectively drive the distal bit 20 at any selected drive ratio and/or may be selectable between multiple drive ratios, and may be disengaged for driving the distal bit 20 at a different drive ratio in order to modify the driving speed for a fastener. In one exemplary arrangement, the detent pin 40 may meshingly engage the gear assembly 52, when in the axial configuration shown in FIG. 1, so as to provide a first drive ratio (e.g., drive ratio=1:3.5—speed driver mode). The drive ratio may include, however, any appropriate ratio greater than 1:1 including about 1:1.1 to about 1:10, and further about 1:3.5 where a full rotation of the handle 12 results in 3.5 rotations of the distal bit 20.

Furthermore, the detent pin 40 may be moved out of engagement with the gear assembly 52 to the T-handle configuration shown in FIG. 2. In the T-handle configuration, a second drive ratio (e.g., drive ratio=1:1—standard mode) can be made. In this way, the driver 10 changes between the first drive ratio and the second drive ratio when changing the configuration of the handle 12 relative to the cap 16 between the axial configuration and the T-handle configuration. This arrangement allows the bit driving tool 10 to be capable of delivering high speed and high efficiency driving (in the axial configuration), while also providing high torque and high precision driving (in the T-handle configuration).

The ratchet assembly 62 may be in communication with the ratchet handle 64 for releasably receiving the distal bit 20. The ratchet assembly 62 may be used to chuck and ratchet the bit 20 as is commonly known in the art. In this way, the bit 20 may be rotated about the tool axis 24 or a securing mechanism (not shown) on the ratchet handle 64 may be engaged for counter-revolution of the distal bit 20.

The bit driving tool 10 may be used for various driving procedures. Exemplary surgical procedures include fastening a locking screw for a femoral prosthesis that can include an intramedullary rod within a femur (FIG. 3), or fastening an acetabular screw within an acetabulum (FIG. 4), for example. As should be understood, various fastener lengths and sizes may use alternate drive speeds for the bit driving tool 10. Accordingly, the drive speeds for the bit driving tool 10 may be altered to achieve the selected driving speeds when inserting the various screws.

With reference to FIG. 3, a femoral prosthesis 70 may be inserted into a prepared femur 72. Various fasteners (e.g., screw 74) may then be used to secure a proximal femoral body prosthesis 76 to a distal femoral prosthesis 73, which can include an intramedullary nail. In one example, distal bit 20 is brought into engagement with the screw 74. The bit driving tool 10 is arranged in the axial configuration, with detent pin 40 in meshed engagement with the gear assembly 52. The ratchet handle 64 is grasped to ratchet the distal bit 20, while the handle 12 is manually rotated around the tool axis 24. The bit driving tool 10 may move the screw 74 at a predetermined drive speed (e.g., one handle turn to three and a half bit/screw turns (1:3.5)) primarily due to engagement with the gear assembly 52. The bit driving tool 10 may advance the screw 74 inwardly of the femoral prosthesis 70 until a desired securement depth is reached. The driver 10 can then be used to fully seat the screw 74 to secure the proximal prosthesis portion 76. The driver 10 can be converted to the T-handle configuration to allow a user to achieve greater torque and precision to ensure proper seating of the screw 74. After fully seating the screw 74, the bit driving tool 10 can be retracted from the femoral prosthesis 70. The bit driving tool 10 can then be used to secure other fasteners (not shown) in connection with the proximal femoral prosthesis 76.

Figure 4:
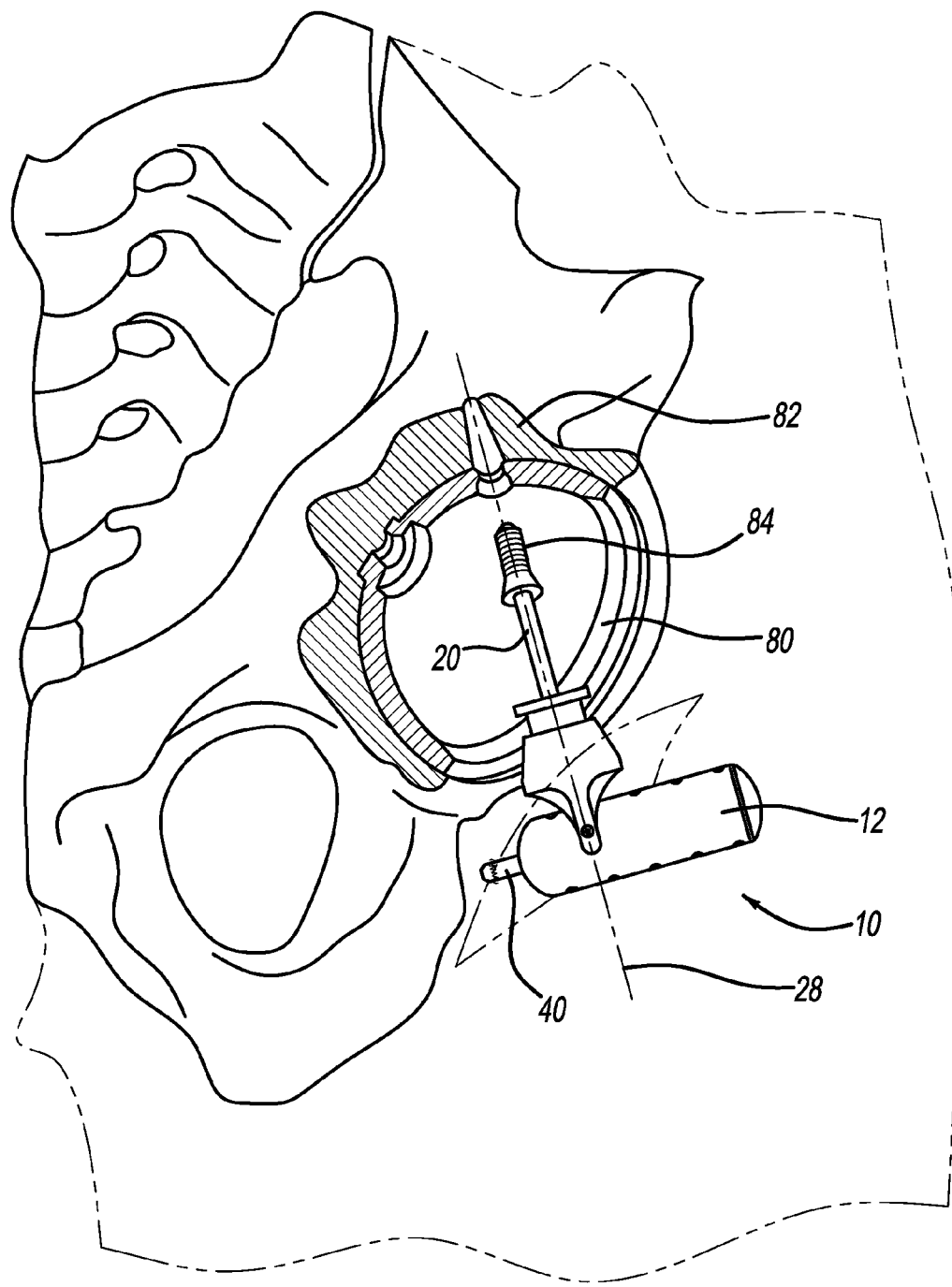
FIG. 4 is a side view of the modular handle of FIG. 2 in an operative position in association with an acetabular prosthesis.

With reference to FIG. 4, an acetabular cup 80 may be inserted into a prepared acetabulum 82. Various fasteners, including a screw 84 may then be used to secure the acetabular cup 80 within the acetabulum 82. In one example, distal bit 20 is brought into engagement with the screw 84. As discussed above, in the axial configuration the driver 10 can provide a 1:3.5 drive ratio. The bit driving tool 10 can then be arranged in the t-handle configuration with detent pin 40 rotated out of engagement with the gear assembly 52. The handle 12 is again manually rotated around the tool axis 24. The bit driving tool 10 may move the screw 84 at a predetermined drive speed (e.g., one handle turn to one driving bit/screw turn (1:1)). The bit driving tool 10 may advance the screw 84 inwardly of the acetabular cup 80 until a desired securement depth is reached. After fully seating the screw 84, the bit driving tool 10 can be retracted from the acetabular cup 80. The bit driving tool 10 can then be used to secure other fasteners (not shown) to retain the acetabular cup 80 or remaining portions of an acetabular prosthesis system (not shown).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A bit driving system, comprising:
a bit to be driven;
a handle extending along a longitudinal axis between a first end and a second end;
a first bit connection portion at least at one of the first end or the second end to selectively engage the handle in a first axial configuration;
a second bit connection portion intermediate the first end and the second end to selectively engage the handle in a second non-axial configuration; and
a gear assembly selectively engaging the handle at the first bit connection portion to provide a first drive ratio for the bit driving system when in the first axial configuration and disengaging the handle at the first bit connection portion to provide a second drive ratio for the bit driving system when in the second non-axial configuration, wherein the first drive ratio is a rotation of the bit relative to the handle and different than the second drive ratio that is also a rotation of the bit relative to the handle.

2. The system of claim 1, wherein the first bit connection portion includes a detent pin protruding a predetermined distance from the handle and selectively retains the handle in the axial configuration.

3. The system of claim 2, wherein the detent pin engages the gear assembly to selectively engage the bit in the first drive ratio relative to the handle.

4. The system of claim 1, wherein the second bit connection portion includes a pivoting mechanism extending transverse to the longitudinal axis at a predetermined distance from the handle first end for selectively retaining the handle in the second non-axial configuration.

5. The system of claim 1, further comprising:
a ratcheting mechanism for ratcheting the bit in the first drive ratio.

6. A bit driving system, comprising:
a handle extending along a longitudinal axis between a first end and a second end;
a pin extending from one of the first end or second end;
a pivoting mechanism protruding from the handle between the first and second ends;
a cap fixedly joined to the handle at the pivoting mechanism; and
a gear assembly in the cap to selectively engage and disengage the pin, wherein the bit driving system provides a first drive ratio for the bit when the pin and gear assembly are engaged and a second drive ratio for the bit when the pin and gear assembly are disengaged.

7. The system of claim 6, wherein the pin extends a predetermined distance from the handle for selectively retaining the handle in an axial configuration.

8. The system of claim 6, wherein the handle pivots around the pivoting mechanism to allow selectively retaining the handle in one of an axial configuration or a T-shaped handle configuration relative to the cap.

9. The system of claim 6, wherein the pivoting mechanism extends transverse to the longitudinal axis at a predetermined distance from the handle first end for selectively retaining the handle in the T-shaped handle configuration.

10. The system of claim 6, further comprising:
a ratcheting mechanism for ratcheting the bit in the first drive ratio when the gear assembly is engaged by the pin.

11. A method for driving a bit with a bit driving tool having a longitudinal axis and a handle with a handle axis rotatable between an axial handle configuration and a non-axial handle configuration, wherein in the axial handle configuration the handle axis extends along the longitudinal axis and in the non-axial handle configuration the handle axis extends transverse to the longitudinal axis, the method comprising:
  selecting one of a first drive ratio or a second drive ratio;
  pivoting the handle of the bit driving tool to the non-axial handle configuration or to the axial handle configuration to achieve the selected drive ratio; and
  rotating the bit driving tool about the longitudinal axis at the selected drive ratio to drive the bit and secure a first fastener.

12. The method of claim 11, further comprising:
  selecting the other of the first drive ratio and the second drive ratio different from the first drive ratio;
  pivoting the handle of the bit driving tool to the other of the non-axial handle configuration or to the axial handle configuration to achieve the selected drive ratio; and
  rotating the bit driving tool about the longitudinal axis at the selected drive ratio to drive the bit and secure at least one of the first fastener or a second fastener.

13. The method of claim 11, further comprising:
  in the axial handle configuration, ratcheting the bit driving tool to secure the first fastener.

14. The method of claim 11, further comprising:
  engaging a securing mechanism on a ratchet handle; and
  ratcheting the first fastener while rotating the bit driving tool about the longitudinal axis.

15. The method of claim 11, wherein pivoting the handle to the axial handle configuration further comprises:
  engaging a detent pin extending from the handle with a gear assembly having a variable drive ratio to drive the bit selectively at the first drive ratio.

16. The method of claim 11, wherein pivoting the handle to the non-axial handle configuration further comprises:
  disengaging the detent pin extending from the handle from the gear assembly; and
  rotating the handle to drive the bit at a second drive ratio.

17. The method of claim 16, wherein the first drive ratio is different from the second drive ratio and the second drive ratio is 1:1.

18. The method of claim 17, further comprising:
  driving the first fastener at the first drive ratio and then driving the first fastener at the second drive ratio.

19. The method of claim 18, wherein the first fastener is an acetabular fixation screw to fix an acetabular cup, and wherein the first drive ratio is operable to turn the screw faster than the second drive ratio.

20. The method of claim 11, wherein pivoting the handle to the non-axial handle configuration further comprises:
  rotating the handle of the bit about a pivoting mechanism extending transverse to the longitudinal axis for selectively retaining the handle in the non-axial handle configuration that substantially represents a T-shaped handle configuration.

* * * * *